United States Patent
Tsai et al.

(10) Patent No.: US 9,995,743 B2
(45) Date of Patent: Jun. 12, 2018

(54) TEST APPARATUS AND PRESSURIZING ASSEMBLY THEREOF

(71) Applicant: HTC Corporation, Taoyuan (TW)

(72) Inventors: Yi-Chin Tsai, Taoyuan (TW); Shih-Jen Lu, Taoyuan (TW); Fu-Cheng Fan, Taoyuan (TW); Ming-Tien Lin, Taoyuan (TW)

(73) Assignee: HTC Corporation, Taoyuan (TW)

( * ) Notice: Subject to any disclaimer, the term of this patent is extended or adjusted under 35 U.S.C. 154(b) by 92 days.

(21) Appl. No.: 14/788,810

(22) Filed: Jul. 1, 2015

(65) Prior Publication Data

US 2017/0003307 A1      Jan. 5, 2017

(51) Int. Cl.
*G01N 31/22* (2006.01)
*G01N 33/543* (2006.01)

(52) U.S. Cl.
CPC ................ *G01N 33/54366* (2013.01)

(58) Field of Classification Search
CPC .................... G01N 33/86; G01N 33/54366
See application file for complete search history.

(56) References Cited

U.S. PATENT DOCUMENTS

| | | | |
|---|---|---|---|
| 6,241,886 B1 | 6/2001 | Kitagawa et al. | |
| 7,932,099 B2 * | 4/2011 | Egan | B01L 3/5023 435/287.1 |
| 2002/0114735 A1 * | 8/2002 | Markart | B01L 3/5023 422/68.1 |
| 2002/0173047 A1 * | 11/2002 | Hudak | B01L 3/5023 436/178 |
| 2003/0064526 A1 * | 4/2003 | Niedbala | A61B 10/0045 436/165 |
| 2004/0182795 A1 | 9/2004 | Dorian et al. | |
| 2008/0145272 A1 * | 6/2008 | Feaster | B01L 3/5023 422/400 |
| 2013/0172780 A1 | 7/2013 | Kuenstner | |
| 2014/0199710 A1 | 7/2014 | Sambursky et al. | |
| 2014/0273549 A1 | 9/2014 | Sauers | |
| 2015/0017068 A1 | 1/2015 | Sturman et al. | |

FOREIGN PATENT DOCUMENTS

| | | |
|---|---|---|
| CN | 1509409 | 6/2004 |
| CN | 102466581 | 5/2012 |
| CN | 1882835 | 7/2012 |

OTHER PUBLICATIONS

"Office Action of Taiwan Counterpart Application," dated Apr. 21, 2016, p. 1-p. 4.

* cited by examiner

*Primary Examiner* — Dennis White
(74) *Attorney, Agent, or Firm* — JCIPRNET

(57) ABSTRACT

A test apparatus including a cassette main body, a test strip and a pressurizing assembly is provided. The cassette main body has a sample entrance. The test strip is disposed in the cassette main body, and the sample entrance of the cassette main body exposes a sample collecting region of the test strip. The pressurizing assembly is detachably combined to the cassette main body, and is adapted to exert a pressure on a liquid sample located at the sample entrance, such that the liquid sample enters the sample collecting region, and reacts with the test strip to display a test result. The test apparatus is able to implement quick and convenience test, by which a complicated pre-processing of a test sample is omitted to save a time and test cost.

20 Claims, 4 Drawing Sheets

# TEST APPARATUS AND PRESSURIZING ASSEMBLY THEREOF

BACKGROUND

Field of the Disclosure

The disclosure relates to a test apparatus and a pressurizing assembly thereof, and particularly relates to a test apparatus adapted to a rapid screening test and a pressurizing assembly thereof.

Description of Related Art

A test cassette adapted to a rapid screening test is positioned to be non-invasive in a medical field, and is an assistant tool to implement fast diagnosis.

In recent years, along with progress of biotechnology, specific antibodies and antigens have been continually developed, so that there are more and more types of cassettes used for implementing rapid screening test for a single disease, which becomes a new trend of in vitro diagnostic medical treatment.

Today, a rapid screening test can be adopted to conduct a human immunodeficiency virus (HIV) test, drug test, flu test, etc. However, since a test sample adapted to the test cassette is still limited to be plasma or serum, it is still required to perform complicated pre-processing to a whole blood sample before the test.

SUMMARY

The disclosure is directed to a test apparatus, which is adapted to conduct a rapid and convenient test, and can even omit complicated pre-processing on a test sample, so as to save a time and cost of the test.

The disclosure provides a test apparatus including a cassette main body, a test strip and a pressurizing assembly. The cassette main body has a sample entrance. The test strip is disposed in the cassette main body, and the sample entrance of the cassette main body exposes a sample collecting region of the test strip. The pressurizing assembly is detachably combined to the cassette main body, and is adapted to exert a pressure on a liquid sample located at the sample entrance, such that the liquid sample enters the sample collecting region, and reacts with the test strip to display a test result.

In an embodiment of the disclosure, the pressurizing assembly includes a base and a pressurizing member. The base is detachably combined to the cassette main body. The pressurizing member is combined to the base to form a sample chamber. The sample chamber is connected to the sample entrance, and the liquid sample is located in the sample chamber, and the pressurizing member is adapted to exert the pressure to the liquid sample, such that the liquid sample enters the sample collecting region of the test strip through the sample entrance.

In an embodiment of the disclosure, the pressurizing assembly further includes a filter film disposed between the base and the cassette main body, and separating the sample entrance and the sample chamber.

In an embodiment of the disclosure, a material of the filter film includes cellulose, plastic, metal or a coagulation material with an OH functional group.

In an embodiment of the disclosure, the pressurizing assembly further includes an elastic member, and the elastic member and the sample entrance are respectively located at two opposite sides of the test strip.

In an embodiment of the disclosure, the cassette main body further has a bottom opening relative to the sample entrance. The bottom opening and the sample entrance are respectively located at two opposite sides of the test strip. The elastic member is located in the bottom opening, and a supporting portion of the base extends into the bottom opening and leans against the elastic member.

In an embodiment of the disclosure, the elastic member is fixed to the supporting portion.

In an embodiment of the disclosure, the pressurizing assembly further includes a protection layer disposed between the elastic member and the test strip for isolating the elastic member and the liquid sample.

In an embodiment of the disclosure, the pressurizing assembly further includes a reaction layer covering the sample collecting region and configured to have a chemical reaction with the liquid sample.

In an embodiment of the disclosure, a material of the reaction layer includes cellulose or a coagulation material with an OH functional group.

In an embodiment of the disclosure, the cassette main body further has an observing window exposing a test result region of the test strip and configured to display the test result.

The disclosure provides a pressurizing assembly adapted to a test cassette to conduct rapid and convenient test, by which a complicated pre-processing on a test sample is omitted, so as to save a time and cost of the test.

The test cassette includes a cassette main body and a test strip. The cassette main body has a sample entrance. The test strip is disposed in the cassette main body, and the sample entrance of the cassette main body exposes a sample collecting region of the test strip. The pressurizing assembly includes a base and a pressurizing member. The base is detachably combined to the cassette main body. The pressurizing member is combined to the base to form a sample chamber. The sample chamber is connected to the sample entrance, and is adapted to accommodate a liquid sample. The pressurizing member is adapted to exert a pressure to the liquid sample, such that the liquid sample enters the sample collecting region of the test strip through the sample entrance, and is reacted with the test strip to display a test result.

In an embodiment of the disclosure, the pressurizing assembly further includes a filter film disposed between the base and the cassette main body, and separating the sample entrance and the sample chamber.

In an embodiment of the disclosure, a material of the filter film includes cellulose, plastic, metal or a coagulation material with an OH functional group.

In an embodiment of the disclosure, the pressurizing assembly further includes an elastic member, and the elastic member and the sample entrance are respectively located at two opposite sides of the test strip.

In an embodiment of the disclosure, the cassette main body further has a bottom opening relative to the sample entrance. The bottom opening and the sample entrance are respectively located at two opposite sides of the test strip. The elastic member is located in the bottom opening, and a supporting portion of the base extends into the bottom opening and leans against the elastic member.

In an embodiment of the disclosure, the elastic member is fixed to the supporting portion.

In an embodiment of the disclosure, the pressurizing assembly further includes a protection layer disposed between the elastic member and the test strip for isolating the elastic member and the liquid sample.

In an embodiment of the disclosure, the pressurizing assembly further includes a reaction layer covering the sample collecting region and configured to have a chemical reaction with the liquid sample.

In an embodiment of the disclosure, a material of the reaction layer includes cellulose or a coagulation material with an OH functional group.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

Figure 1:
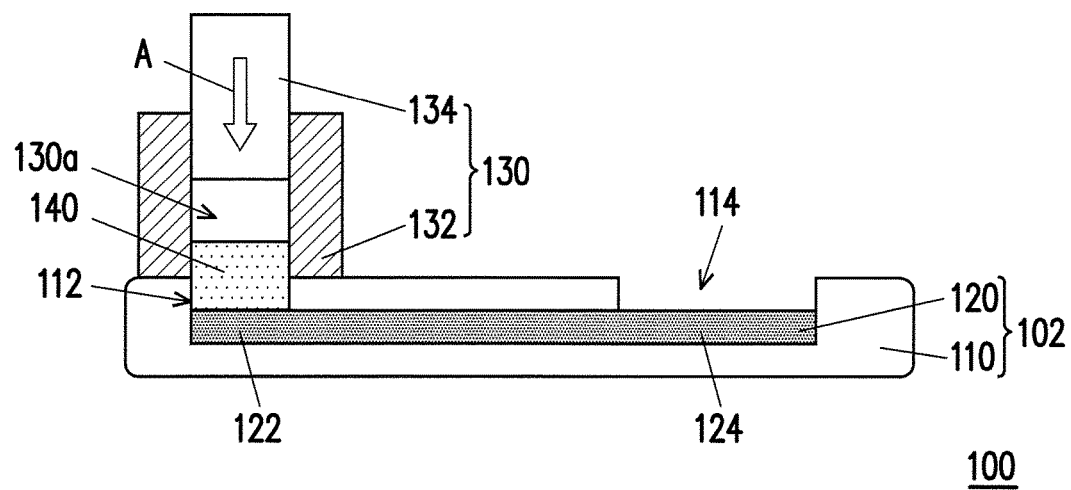
FIG. 1 is a schematic diagram of a test apparatus according to an embodiment of the disclosure.

In following embodiments, a test apparatus composed of a pressurizing assembly and a test cassette is taken as an example for descriptions. Actually, the pressurizing assembly of the disclosure can be adapted to different test cassettes, which is not limited to the following embodiments.

Moreover, in the following descriptions, a blood test is taken as an example to introduce the rapid screening test of the test apparatus. However, the test sample adapted to the test apparatus and the pressurizing assembly of the disclosure is not limited to blood, and a water sample for a water quality test, a urine sample for a urine test, etc., are all adapted to the design of the disclosure.

To facilitate description, in the following embodiments of the disclosure, the same or similar devices are denoted by similar reference numerals. For example, regarding a same or similar device A, in different embodiments, the referential numbers thereof are probably 108, 208, 308, etc., and thus descriptions of the same or similar devices are not repeated. Those skilled in the art may refer to the context and descriptions of the related embodiments for a clear understanding and implementation.

FIG. 1 is a schematic diagram of a test apparatus 100 according to an embodiment of the disclosure. Referring to FIG. 1, the test apparatus 100 includes a pressurizing assembly 130 and a test cassette 102 adapted to the pressurizing assembly 130. The test cassette 102 includes a cassette main body 110 and a test strip 120. The cassette main body 110 has a sample entrance 112 and an observing window 114. The test strip 120 is disposed in the cassette main body 110, and the sample entrance 112 and the observing window 114 of the cassette main body 110 respectively exposes a sample collecting region 122 and a test result region 124 of the test strip 120.

Moreover, the pressurizing assembly 130 is detachably combined to the cassette main body 110. In the present embodiment, the pressurizing assembly 130 includes a base 132 and a pressurizing member 134. The base 132 is detachably combined to the cassette main body 110, which is, for example, assembled to one end of the cassette main body 110 through a mechanical design such as screwing or tightening, etc. or other possible manner, and corresponds to the sample entrance 112 of the cassette main body 110, though the disclosure is not limited thereto.

The pressurizing member 134 is, for example, a piston, which is combined with the base 132, and can move relative to the base 132. After the pressurizing assembly 130 is combined with the cassette main body 110, a sample chamber 130*a* can be formed above the sample entrance 112. The pressurizing assembly 130 and the cassette main body 110 are preferably combined closely, i.e., the sampling chamber 130*a* has a semi-sealing (or almost sealing) state, such that when the pressurizing member 134 moves along a direction A, an air pressure in the sample chamber 130*a* can be increased along with volume reduction of the sample chamber 130*a*. Moreover, the pressurizing member 134 can be driving through a manual or automation system.

In the present embodiment, the sample chamber 130*a* is directly connected to the sample entrance 112 of the cassette main body 110. Therefore, when the sample chamber 130*a* contains a liquid sample 140, for example, plasma or serum, etc., and the pressurizing member 134 moves along the direction A to exert a pressure on the liquid sample 140, the liquid sample 140 enters the sample collecting region 122 of the test strip 120 through the sample entrance 112, and reacts with the test strip 120 to display a test result at the test result region 124. The test result region 124 is, for example, a color display region, and the user can observe a test result through the observing window 114 by eyes. Alternatively, an automation system can be adopted to obtain the test result through an image detection device or other equipment.

Therefore, in the present embodiment, the test cassette 102 is used in collaboration with the pressurizing assembly 130, and the pressurizing assembly 130 can exert a pressure on the liquid sample 140 to speed up or force the liquid sample 140 to enter the test cassette 102, so as to implement rapid and convenient test.

Figure 2:
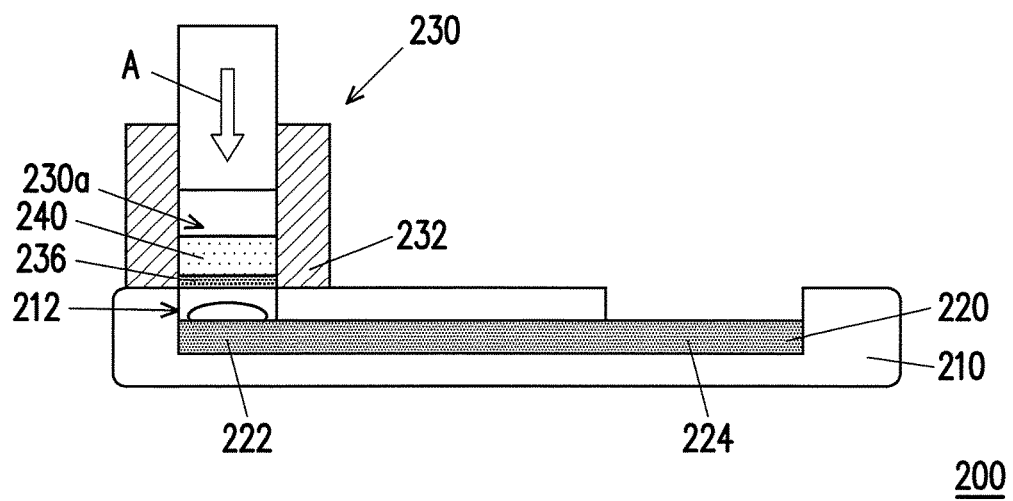
FIG. 2 is schematic diagram of a test apparatus according to another embodiment of the disclosure.

FIG. 2 is schematic diagram of a test apparatus 200 according to another embodiment of the disclosure. As shown in FIG. 2, compared to the test apparatus 100 of FIG. 1, the pressurizing assembly 230 of the present embodiment further includes a filter film 236 disposed between the base 232 and the cassette main body 210, which is used for separating the sample entrance 212 and the sample chamber 230*a*. In this way, when the pressurizing assembly 230 exerts a pressure to the liquid sample 240 in the sample chamber 230*a*, the liquid sample 240 first passes through the filter film 236, and then enters the sample entrance 212 of the cassette main body 210.

Therefore, in the present embodiment, a material of the filter film 236 can be selected according to a test requirement and a type of the liquid sample 240, such that the filter film 236 can filter the liquid sample 240. In this way, a complicated pre-processing performed on the test sample 240 before the test can be omitted, so as to save time and test cost. The material of the filter film 236 may include plastic, metal or a coagulation material with an OH functional group. To be specific, plastic or metal can be taken as a base material of the filter film 236, and chemical processing (for example, etching) or mechanical processing (for example, laser drilling) can be performed to the base material to form a porous film. Alternatively, the filter film 236 can also be cellulose or a coagulation material with an OH functional group.

For example, the test apparatus 200 of the present embodiment may adopt cellulose or a coagulation material with an OH functional group to serve as a filter film, so as to directly test a whole blood. During the operation, the whole blood serving as the liquid sample 240 can be directly put into the sample chamber 230a, and the pressurizing assembly 230 is made to move along the direction A, such that the pressurizing assembly 230 exerts a pressure on the whole blood serving as the liquid sample 240. After the liquid sample 240 passes through the filter film 236 having a coagulation effect, coagulation factors such as blood cells or even fibrinogen, etc. in the whole blood are filtered. The remained plasma or serum enters the sample entrance 212 of the cassette main body 210, and enters the sample collecting region 222 of the test strip 220 through the sample entrance 212, and further reacts with the test strip 220 to display a test result at the test result region 224.

In other words, the test apparatus 200 of the present embodiment is quite suitable to serve as a home care or non-clinical quick diagnosis tool. Taking the blood test as an example, after blood collection, the user is unnecessary to perform the complicated pre-processing to the blood to separate the plasma or serum, but directly puts the collected blood into the sample chamber 230a of the test apparatus 200 of the present embodiment to carry on the blood test.

Similarly, the test apparatus 200 of the present embodiment can also be applied to different test environments such as a water quality test, a urine test, etc., where the filter film 236 can be used to filter a specific impurity to obtain a correct test result.

Since the test apparatus 200 of the present embodiment can direct process (for example, filter) the liquid sample through the filter film, the complicated pre-processing of the test sample before the test can be omitted, so as to save the time and test cost.

Figure 3:
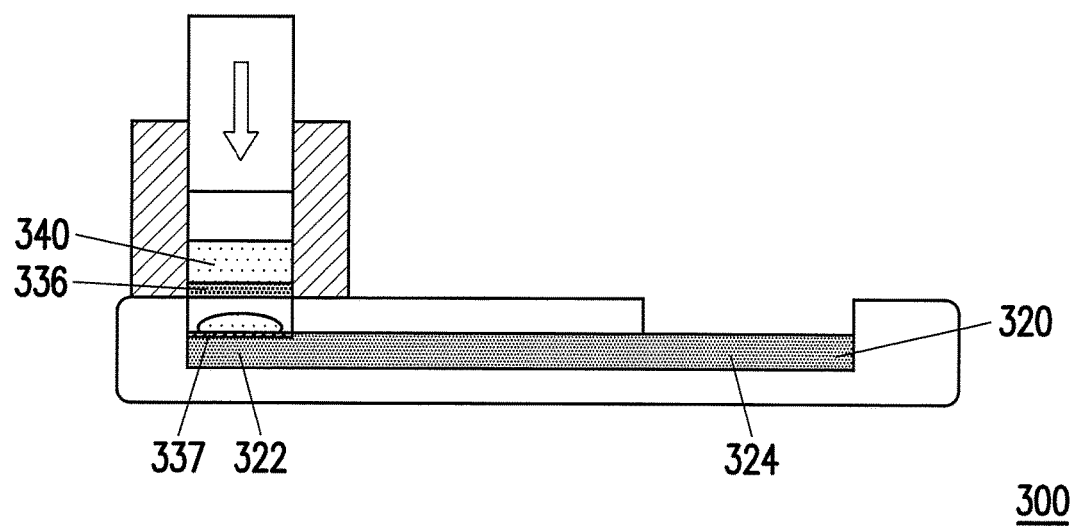
FIG. 3 is a variation of the test apparatus of FIG. 2.

FIG. 3 is a variation of the test apparatus 200 of FIG. 2. During the blood test, since it is not limited to combine a mechanism of the coagulation effect with the filter film, i.e., it is unnecessary to use a coagulation material to serve as the filter film, the mechanism with the coagulation effect can be set on the sample collecting region of the test strip.

To be specific, compared with the test apparatus 200 of FIG. 2, the test apparatus 300 of the present embodiment further includes a reaction layer 337 covering the sample collecting region 322 of the test strip 320, and the reaction layer 337 and the liquid sample 340 may have a chemical reaction. For example, in the blood test, a material of the reaction layer 337 includes cellulose or a coagulation material with an OH functional group. In this way, after the whole blood serving as the liquid sample 340 passes through the reaction layer 337, the coagulation factors such as blood cells or even fibrinogen, etc. in the whole blood are filtered. The remained plasma or serum enters the sample collecting region 322 of the test strip 320, and further reacts with the test strip 320 to display a test result at the test result region 324.

In the present embodiment, the filter film 336 can be omitted, or the design of the embodiment of FIG. 2 can be adopted to maintain the filter film 336, such that the liquid sample 340 sequentially passes through the filter film 336 and the reaction layer 337 to enter the sample collecting region 322 of the test strip 320.

Figure 4:
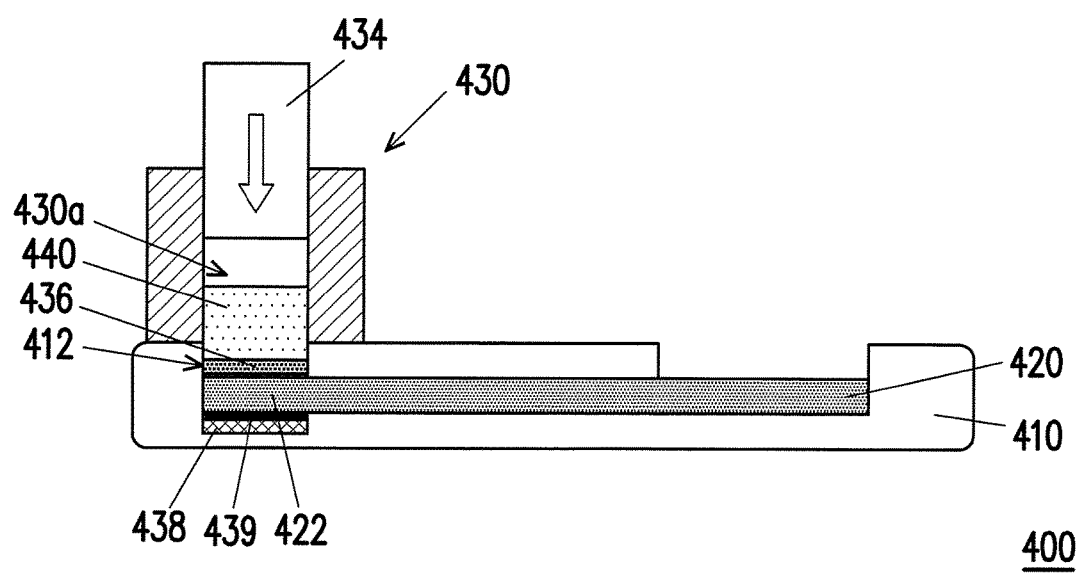
FIG. 4 is a schematic diagram of a test apparatus according to another embodiment of the disclosure.

FIG. 4 is a schematic diagram of a test apparatus 400 according to another embodiment of the disclosure. As shown in FIG. 4, compared with the test apparatus 200 of FIG. 2, the pressurizing assembly 430 of the present embodiment further includes an elastic member 438 under the test strip 420, where the elastic member 438 and the sample entrance 412 of the cassette main body 410 are respectively located at two opposite sides of the test strip 420. Moreover, the filter film 436 is located in the sample entrance 412, and is close to the sample collecting region 422 of the test strip 420. A material of the elastic member 438 includes plastic, rubber or a metal material. To be specific, the elastic member 438 is, for example, a block body made of a flexible plastic material or a flexible rubber material, or is composed of a metal spring and a plate.

When the pressurizing member 434 of the pressurizing assembly 430 exerts a pressure on the liquid sample 440 in the sample chamber 430a, the elastic member 438 located at a backside of the test strip 420 can provide a reaction force to the test strip 420, such that the test strip 420 and the filter film 436 can keep a close contact. In this way, a capillary action between the test strip 420 and the filter film 436 can assist the liquid sample 440 to smoothly pass through the filter film 436 to reach the sample collecting region 422 of the test strip 420.

Moreover, a protection layer 439, for example, a water-resisting layer can be further configured between the elastic member 438 and the test strip 420 for isolating the elastic member 438 and the liquid sample 440, so as to avoid a situation that the liquid sample 440 infiltrates the elastic member 438 or is contaminated by the elastic member 438.

Figure 5A:
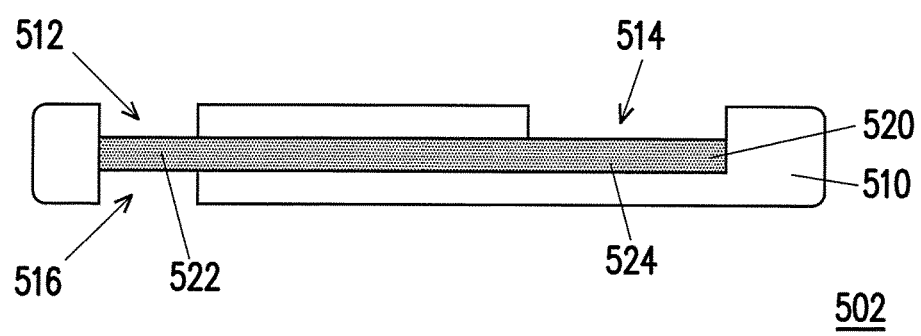
FIGS. 5A-5C are schematic diagrams of a test apparatus and a test method thereof according to another embodiment of the disclosure.
Figure 5B:
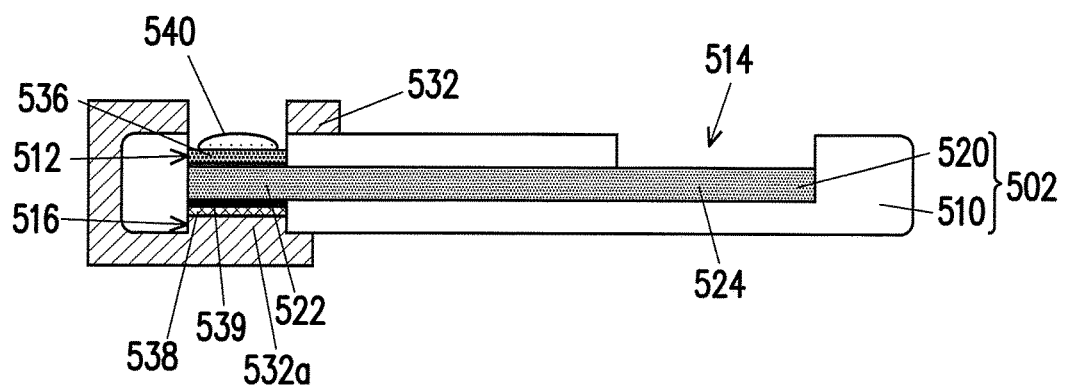
Figure 5C:
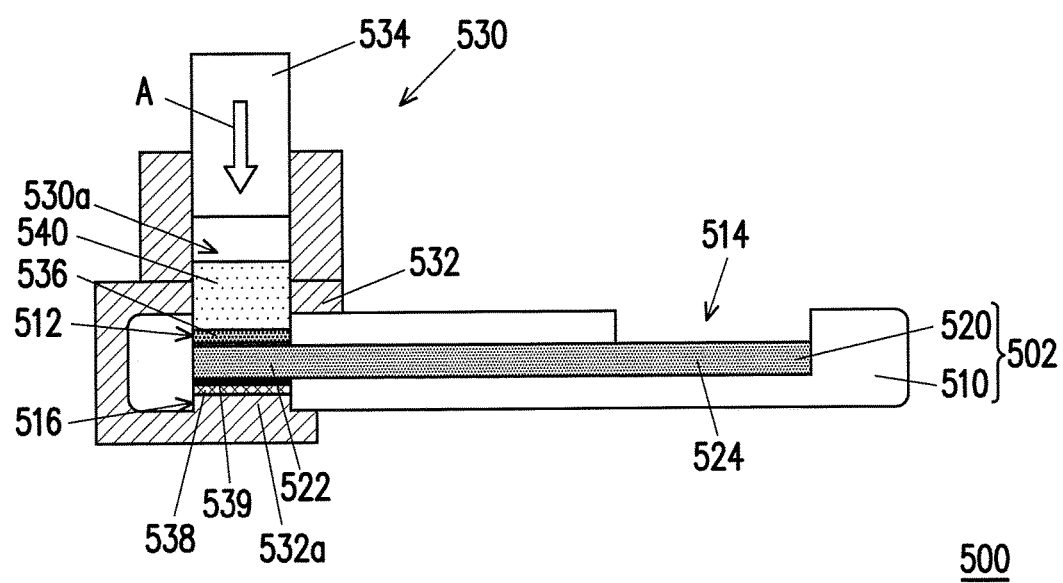

FIGS. 5A-5C are schematic diagrams of a test apparatus 500 and a test method thereof according to another embodiment of the disclosure. Compared with the aforementioned embodiments, in the present embodiment, structures and a combination method of the base 532 of the pressurizing assembly 530 and the cassette main body 510 are changed.

To be specific, FIG. 5A illustrates the test cassette 502 of the present embodiment. Besides the sample entrance 512 and the observing window 514, the cassette main body 510 further has a bottom opening 516 relative to the sample entrance 512. The bottom opening 516 and the sample entrance 512 are respectively located at two opposite sides of the test strip 520.

Moreover, as shown in FIG. 5B, the base 532 is clamped to one end of the cassette main body 510 through mechanism tightening. The filter film 536 is located in the sample entrance 512, and is close to the sample collecting region 522 of the test strip 520. The elastic member 538 is located in the bottom opening 516, and a supporting portion 532a of the base 532 extends into the bottom opening 516 and leans against the elastic member 538, such that the elastic member 538 and the filter film 536 are respectively located two opposite sides of the test strip 520. The elastic member 538 can be fixed to the supporting portion 532a through, for example, adhesion bonding.

During the test, as shown in FIG. 5C, the user can first put in the liquid sample 540, and combine the pressurizing member 534 with the base 532, such that the liquid sample 540 is located in the sample chamber 530a. Thereafter, the pressurizing member 534 moves along the direction A to exert a pressure on the liquid sample 540, such that the liquid sample 540 can pass through the filter film 536 located at the sample entrance 512 to enter the sample collecting region 522 of the test strip 520. After the liquid sample 540 reacts with the test strip 520, a test result is displayed at the test result region 524.

In the present embodiment, when the pressurizing member 534 of the pressurizing assembly 530 exerts the pressure on the liquid sample 540 in the sample chamber 530a, the elastic member 538 located at the backside of the test strip 520 can provide a reaction force to the test strip 520, such that the test strip 520 and the filter film 536 can keep a close contact. Moreover, a capillary action between the test strip 520 and the filter film 536 can assist the liquid sample 540 to smoothly pass through the filter film 536 to reach the sample collecting region 522 of the test strip 520.

Similar to the embodiment of FIG. 4, in the present embodiment, the protection layer 539 can be further configured between the elastic member 538 and the test strip 520 for isolating the elastic member 538 and the liquid sample 540, so as to avoid a situation that the liquid sample 540 infiltrates the elastic member 538 or is contaminated by the elastic member 538.

Moreover, the characteristics disclosed in the aforementioned embodiments can be suitably combined or changed in possible cases. For example, the reaction layer 337 of the embodiment of FIG. 3 can be applied to the embodiments of FIG. 1/4/5 to locate on the sample collecting region 322/422/522 of the test strip 320/420/520. Details thereof are not repeated.

In summary, the disclosure provides the pressurizing assembly adapted to the test cassette, the pressurizing assembly is used to exert a pressure to the liquid sample to speed up or force the liquid sample to enter the test cassette, so as to implement rapid and convenient test. Moreover, the pressurizing assembly of the disclosure may also have the filter film located between the base and the cassette main body, the filter film separates the sample entrance and the sample chamber, such that when the liquid sample in the sample chamber is pressed, the liquid sample first passes through the filter film, and then enter the sample entrance of the cassette main body. In other words, the filter film is used to filter the liquid sample, so that the complicated pre-processing performed on the test sample before the test can be omitted, so as to save the time and test cost.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A test apparatus, comprising:
   a cassette main body, having a sample entrance;
   a test strip, disposed in the cassette main body, wherein the sample entrance of the cassette main body exposes a sample collecting region of the test strip; and
   a pressurizing assembly, detachably combined to the cassette main body, and adapted to exert a pressure on a liquid sample located at the sample entrance, such that the liquid sample enters the sample collecting region, and reacts with the test strip to display a test result, wherein the pressurizing assembly has an elastic member, the elastic member being located under the test strip and corresponding to the sample entrance of the cassette main body.

2. The test apparatus as claimed in claim 1, wherein the pressurizing assembly comprises:
   a base, detachably combined to the cassette main body; and
   a pressurizing member, combined to the base to form a sample chamber, wherein the sample chamber is connected to the sample entrance, the liquid sample is located in the sample chamber, and the pressurizing member is adapted to exert the pressure to the liquid sample, such that the liquid sample enters the sample collecting region of the test strip through the sample entrance.

3. The test apparatus as claimed in claim 2, wherein the pressurizing assembly further comprises:
   a filter film, disposed between the base and the cassette main body, and separating the sample entrance and the sample chamber.

4. The test apparatus as claimed in claim 3, wherein a material of the filter film comprises plastic, metal or a coagulation material with an OH functional group.

5. The test apparatus as claimed in claim 1, wherein the elastic member and the sample entrance are respectively located at two opposite sides of the test strip.

6. The test apparatus as claimed in claim 5, wherein the cassette main body further has a bottom opening relative to the sample entrance, the bottom opening and the sample entrance are respectively located at two opposite sides of the test strip, the elastic member is located in the bottom opening, and a supporting portion of the base extends into the bottom opening and leans against the elastic member.

7. The test apparatus as claimed in claim 6, wherein the elastic member is fixed to the supporting portion.

8. The test apparatus as claimed in claim 5, wherein the pressurizing assembly further comprises:
   a protection layer, disposed between the elastic member and the test strip, and configured to isolate the elastic member and the liquid sample.

9. The test apparatus as claimed in claim 1, wherein the pressurizing assembly further comprises:
   a reaction layer, covering the sample collecting region, and configured to have a chemical reaction with the liquid sample.

10. The test apparatus as claimed in claim 9, wherein a material of the reaction layer comprises a coagulation material with an OH functional group.

11. The test apparatus as claimed in claim 1, wherein the cassette main body further has an observing window exposing a test result region of the test strip and configured to display the test result.

12. A pressurizing assembly, adapted to a test cassette, wherein the test cassette comprises:
   a cassette main body, having a sample entrance; and
   a test strip, disposed in the cassette main body, and the sample entrance exposes a sample collecting region of the test strip, the pressurizing assembly comprising:
   a base, detachably combined to the cassette main body;
   an elastic member, the elastic member being located under the test strip and corresponding to the sample entrance of the cassette main body; and
   a pressurizing member, combined to the base to form a sample chamber, wherein the sample chamber is connected to the sample entrance, and is adapted to accommodate a liquid sample, the pressurizing member is adapted to exert a pressure to the liquid sample, such that the liquid sample enters the sample collecting region of the test strip through the sample entrance, and is reacted with the test strip to display a test result.

13. The pressurizing assembly as claimed in claim 12, further comprising:
   a filter film, disposed between the base and the cassette main body, and separating the sample entrance and the sample chamber.

14. The pressurizing assembly as claimed in claim 13, wherein a material of the filter film comprises plastic, metal or a coagulation material with an OH functional group.

15. The pressurizing assembly as claimed in claim 12, wherein the elastic member and the sample entrance are respectively located at two opposite sides of the test strip.

16. The pressurizing assembly as claimed in claim 15, wherein the cassette main body further has a bottom opening relative to the sample entrance, the bottom opening and the sample entrance are respectively located at two opposite sides of the test strip, the elastic member is located in the bottom opening, and a supporting portion of the base extends into the bottom opening and leans against the elastic member.

17. The pressurizing assembly as claimed in claim 16, wherein the elastic member is fixed to the supporting portion.

18. The pressurizing assembly as claimed in claim 15, further comprising:
   a protection layer, disposed between the elastic member and the test strip, and configured to isolate the elastic member and the liquid sample.

19. The pressurizing assembly as claimed in claim 12, further comprising:
   a reaction layer, covering the sample collecting region, and configured to have a chemical reaction with the liquid sample.

20. The pressurizing assembly as claimed in claim 19, wherein a material of the reaction layer comprises a coagulation material with an OH functional group.

* * * * *